United States Patent [19]

Connemann et al.

[11] Patent Number: 5,354,878

[45] Date of Patent: Oct. 11, 1994

[54] PROCESS FOR THE CONTINUOUS PRODUCTION OF LOWER ALKYL ESTERS OF HIGHER FATTY ACIDS

[76] Inventors: Joosten Connemann, Sagemuhlenstrabe 45, 2950 Leer; Anton Krallmann, Zeisigstrabe 6, 2953 Rhauderfehn; Erich Fischer, Gerhard-Hauptmann-Strabe 82, 2956 Moomerland-Warsingsfehn, all of Fed. Rep. of Germany

[21] Appl. No.: 37,224

[22] Filed: Mar. 26, 1993

[30] Foreign Application Priority Data

Mar. 26, 1992 [DE] Fed. Rep. of Germany ....... 4209779

[51] Int. Cl.$^5$ .............................................. C07C 51/00
[52] U.S. Cl. .................... 554/167; 554/168; 554/161
[58] Field of Search ............................... 554/168, 167

[56] References Cited

U.S. PATENT DOCUMENTS

5,116,546  5/1992  Klok et al. ........................... 554/167

FOREIGN PATENT DOCUMENTS

517818 10/1955 Canada .

*Primary Examiner*—José G. Dees
*Assistant Examiner*—Dwayne C. Jones
*Attorney, Agent, or Firm*—Ostrolenk, Faber, Gerb & Soffen

[57] ABSTRACT

Production of lower alkyl esters of higher fatty acids from an oil phase and lower alcohols by catalytic transesterification at reaction temperatures of up to 100° C. in the presence of an alkaline catalyst, includes a) introducing a mixture of oil phase, alcohol and catalyst at reaction temperature into the top of a first reactor column, at a rate of flow which is lower than the sinking rate of the glycerine separated from the reaction mixture, b) the reaction mixture is passed into a second reactor for further transesterification, c) the thus obtained reaction mixture is further freed of glycerine in an initial separating stage by means of a short-term washing, d) the reaction mixture is passed into a third reactor with addition of further alcohol and catalyst, and at a rate of flow conforming to the first stage of the process, e) the reaction mixture is further transesterified, f) reaction product is freed of the remaining methanol, glycerine, soaps formed and catalyst in a second separating stage, under addition of an aqueous extraction buffer solution, and g) the reaction mixture is freed of lower alcohols by stripping, washed with suitable extraction and washing solutions and dried.

16 Claims, 1 Drawing Sheet

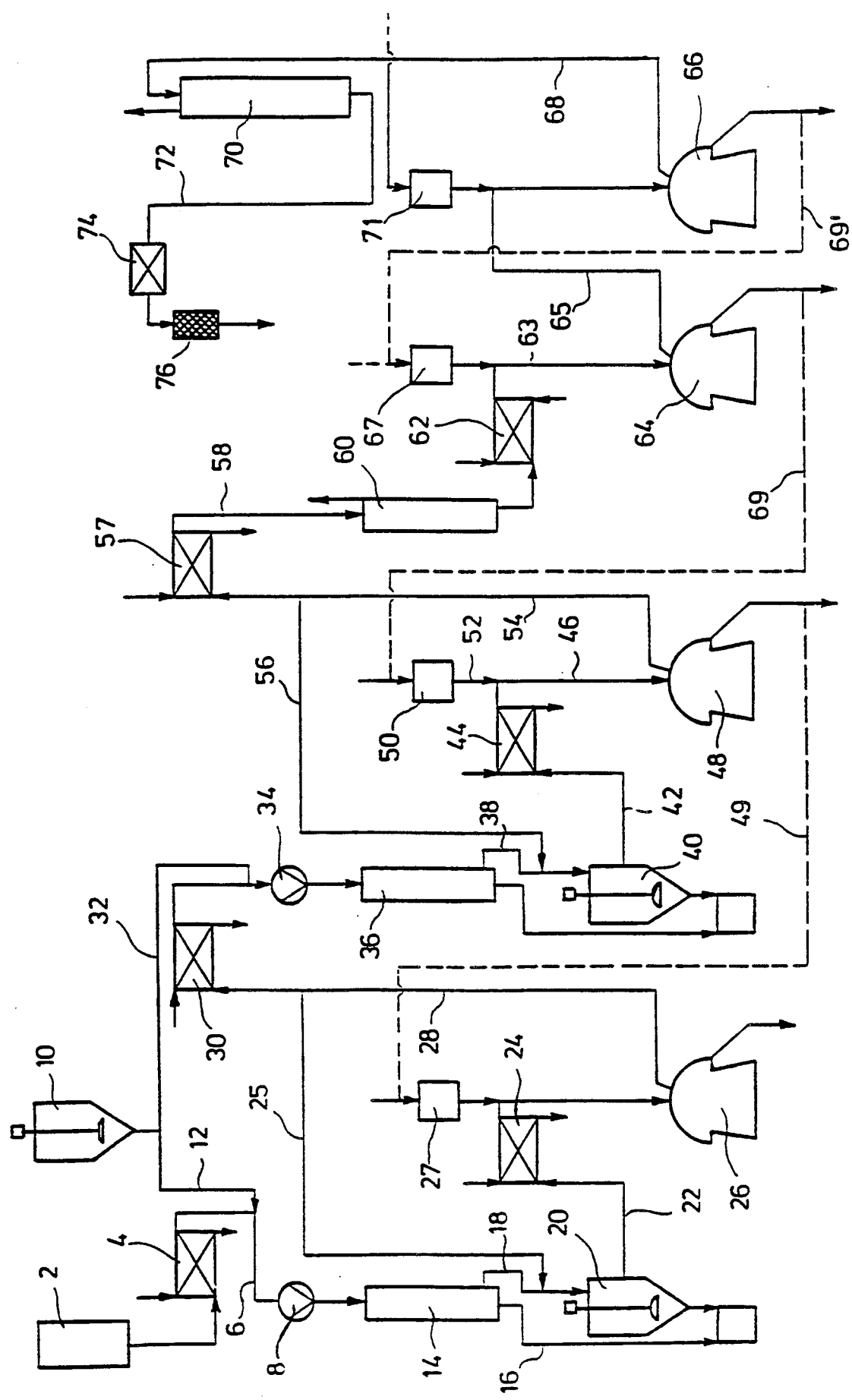

PROCESS FOR THE CONTINUOUS PRODUCTION OF LOWER ALKYL ESTERS OF HIGHER FATTY ACIDS

BACKGROUND OF THE INVENTION

The present invention concerns a process for the continuous production of lower ($C_1$ to $C_4$) alkyl esters of higher fatty acids by means of an essentially ambient pressure, catalytic transesterification process applied to an oil phase containing higher ($C_6$ to $C_{24}$) fatty acid triglycerides or natural oils or fats containing free fatty acids, and of $C_1$ to $C_4$ alcohols. The process is effected at reaction temperatures of up to 100° C. in the presence of an alkaline catalyst, followed by separating glycerine, removing the catalyst residue and stripping off the lower alcohols.

This kind of continuous process is known, e.g. from FR-PS 2 560 210 or DE-OS 34 44 893 and in these methods, transesterifications of up to 95% and 97%, respectively, are obtained. Higher degrees of transesterification—about 98%—are obtained with a multistage process in accordance with FR-PS 2 577 569 or EP-B-O 127 104, which are carried out at pressures of up to 5 bars, in the presence of a liquid means of extraction. To obtain a higher output, the transesterification process can be carried out according to e.g. EP-A2-0 198 243 at higher temperatures of 210° to 280° C. and at 60 to 80 bars, with long reaction periods. In still other methods, e.g. in accordance with EP-B-10 192 035, ion exchangers are introduced as catalysts for pre-transesterification, or the ester phases are washed by means of cation exchangers, e.g. in accordance with OE-PS 386222.

All these methods have the disadvantage that they are not economical because they require the use of high temperature or pressure, a long reaction period or a high apparatus volume, or when a transesterification of up to 97.5 to 98.7% is obtained there is too large a portion of bound or, above all, free glycerine, and the acid value is too high, which requires expending a considerable amount of time and energy into separating the remaining glycerine and the resulting soaps and fatty acids, for example by means of an additional, final purification by distillation.

The suggestion was made in accordance with DE-PS 39 32 514 to introduce pipe reactors with additional static separators, whereby the reaction is carried out at very high rates of flow. This kind of method has become interesting of late because the fatty acid esters on their own, or together with methanol or gas oil, are suitable as fuel for diesel motors, as described in DE-OS 37 27 081 and further literature named therein.

The latest tests carried out by motor manufacturers show that it is important for the finished ester mixture which is used as high grade diesel fuel after transesterification to have a total glycerine content of under 0.20% of weight and preferably under 0.15% of weight. The free glycerine content should be under 0.01% by weight, the acid value should not be more than 0.2 and the triglyceride residue content should tend towards nil.

Up to now, these values could only be approximately obtained by means of a final purification by distillation, whereas the transesterification methods mentioned above, without a distillation step, just about meet the Austrian norm C 1190 which specifies a maximum of 0.25% total glycerine, 0.03% free glycerine and an acid value of 1.0.

All methods mentioned so far are based on the fact that esters suitable for use as diesel fuel are manufactured by transesterification (alcoholysis) of all sorts of vegetable fats and oils with lower aliphatic alcohols. For example, sunflowerseed oil, soya bean oil, corn oil, cottonseed oil, almond oil, groundnut oil, palm oil, coconut oil, linseed oil, and castor oil, and especially rapeseed oil, are considered appropriate. Transesterification is carried out with a suitable monovalent alcohol such as ethanol, isopropanol, butanol, or multivalent alcohols such as trimethylolpropane, but especially with methanol in the presence of a transesterification catalyst, e.g. metal alcoholoates, metal hydrides, metal carbonates, metal acetates or various acids, especially with sodium alkoxide or hydroxide or potassium hydroxide.

The object of the present invention is to provide a new method of the kind mentioned above, which can be carried out continuously and economically, whilst bringing about a transesterification of over 99.2 and up to 99.6%, and especially separating off the glycerine quickly and almost entirely, whilst avoiding to a large extent the formation of soaps, which would reduce the output.

BRIEF DESCRIPTION OF THE DRAWING

The FIGURE shows a schematic representation of the reaction apparatus.

DESCRIPTION OF THE INVENTION

In accordance with the invention, a transesterification of lower alcohol with higher fatty acid materials is carried out at ambient pressure and a temperature of up to 100° C. in the presence of an alkaline catalyst using a multistage process in which a first stage transesterification is effected in a column where the reaction mixture rate of flow is less than the rate of separated glycerine removal from the column, followed by a second stage transesterification and extraction, and then the two stages are repeated. Details of the process are described below.

The invention will be further explained in connection with the flow scheme of the sole FIGURE. Basically, the first stage of this method involves introducing a reaction mixture I, which is a pre-mixed combination of oil phase, alcohol and catalyst, at reaction temperature into the top of a standing column used as a first reactor, such that the rate of flow is lower than the sinking rate of the glycerine that separates from reaction mixture I, obtained in the direction of flow. This glycerine is withdrawn continuously and a transesterification of about 85 to 90% is realized in the standing column.

The vegetable oil, here rapeseed oil, coming out of supply tank 2 is passed at a rate of 57 l/h through a heat exchanger 4, where it is warmed to a reaction temperature of less than 100° C., e.g. between 60° and 75° C., and passes through line 6 together with the alcohol and a catalyst into mixer 8, which is set up as a static, but preferably dynamic, mixer.

Methanol is stored in a supply vessel 10 with a content of 168 l, together with 2 to 3 kg NaOH. The methanol/alkali mixture, representing a surplus of 1.4 to 1.6 times methanol with 0.24 to 0.36% of weight NaOH are passed via pipe 12 at the rate of 10 l/h into mixer 8.

Reaction mixture I is passed into the top of the first reactor 14, set up as a standing column, at a lower rate of flow than the sinking rate of the glycerine being separated off in the direction of flow. The glycerine formed during this transesterification can be removed via a pipe 16 continuously or discontinuously. Surprisingly, a transesterification of 85 to 90% already takes place in this column. The product reaction mixture I, containing lower alkyl esters, monoalcohols, catalyst, oil and partially transformed oil, and which still contains about 0.5% of weight dissolved and dispersed glycerine, is passed via a pipe 18, just above the bottom of column 14 into a second reactor 20, set up as a stirring reactor, where further transesterification—up to approximately 95 to 97%—takes place over a residence time of 2 minutes to 2 hours, preferably one hour at reaction temperatures of 60° to 80° C.

In a first separating stage, the thus obtained reaction mixture II is freed of further glycerine. This can take place in one of two ways: either reaction mixture II is passed from stirring reactor 20 via a pipe 22 into separator 26 by means of a heat exchanger 24 at a temperature of 20° to 40° C., preferably 25° to 30° C. or it is brought up to a temperature of 70° to 90° C. in heat exchanger 24 and passed into separator 26, under addition of 0.25 to 10% of weight hot, aqueous extraction solution from supply 27. This highly efficient separator is preferably set up as a plate separator, which not only separates phases of different densities, but allows at the same time a short-term extraction (e.g., about 1–20 seconds) of the light ester phase with added aqueous phase, almost entirely extracting the dissolved glycerine, which would hinder a shift of balance, whilst avoiding additional saponification. Reaction mixture II can be introduced at a rate of 50 l/h.

The light phase can be partially passed back on to the preconnected stirring reactor in the cycle, via pipe 25, and reduce the glycerine content there considerably.

If reaction mixture II is passed into the separator at a temperature of 20° to 40° C., about a further 1% by weight of glycerine is removed, while if the hot reaction mixture II is passed in under addition of a hot, aqueous extraction solution, about 1 to 2.5% by weight of further glycerine is removed, creating the conditions for subsequent, additional transesterification.

In a further stage of the process, the thus obtained reaction mixture II is passed into a third reactor, set up as a standing column, at reaction temperature. Also added, preferably in countercurrent flow, is further lower alcohols and catalyst and at a rate of flow corresponding to the first stage of the process.

For this, reaction mixture II or the transesterification product respectively is passed into a heat exchanger 30 via pipe 28 at a rate of 50 l/h, where a temperature of 70° to 90° C. is established, and then into mixing pump 34, where at the same time a mixture of to 0.11% NaOH and an 0.2 to 0.4-fold surplus of alcohol from supply vessel 10 (containing alcohol and sodium hydroxide) is being passed in via pipe 32 at a rate of 1.5 to 3 l/h. The resulting mixture is passed to a third reactor 36, also set up as a standing column and in which further transesterification, to a degree of 98.5 to 99%, takes place. The rate of flow here, too, is kept lower than the sinking rate of the glycerine being separated off from the reaction mixture. Reaction mixture III, taken from the bottom of the column, is passed via pipe 38 into a second stirring reactor 40, where it is transesterified further at temperatures of 60° to 80° C. and a residence time of 0.5 to 2 hours, but preferably at a temperature of 65° to 68° C. and with a residence time of one hour.

The product emanating from this stirring reactor is passed over a pipe 42 into heat exchanger 44, and then in a further separating step at temperatures of 70° to 90° C. via pipe 46 into a further separator 48, which is set up analogously to the first separator 26. This separator is fed via pipe 52 with a hot, aqueous buffer solution (e.g. pH about 8–10) or aqueous extraction solution out of a supply vessel 50, analogously to one variation of the first separation step. For this, sodium hydroxide, any soap formed and glycerine are stripped off by the water, whereby the thus obtained reaction mixture IV is passed off via a pipe 54 for further washing, whilst part of this reaction product is passed back into the second stirring reactor 40 via pipe 56. The concentration of dissolved glycerine is thus reduced proportionally also in the second stirring reactor 40, in order to shift the reaction equilibrium and thus obtain a higher degree of transesterification. Reaction product IV, now passed on for further washing, has a degree of transesterification of 99.2 to 99.6%, and contains no more than approximately 500 to 800 ppm soap, plus a little methanol and water.

In order to remove the remaining methanol, reaction product IV is then passed via pipe 58, over heat exchanger 57 into a stripping column 60, which is heated and runs in a slight vacuum, so that the ester phase shows a methanol content distinctly lower than 0.1% on leaving the column. The evaporated methanol is passed into a condensation system (not shown), to which all columns and stirring vessels are connected, condensed there and passed back via an adequate rectification in the cycle to the attached catalyst vessel 10.

Reaction mixture IV is then passed on to the first washing stage, where it is brought up to a temperature of about 80° to 90° C. by heat exchanger 62, then passed with water at about 80° to 90° C. at a rate of 2 to 10 l/h via pipe 63 into a further separator 64, where catalyst residue, water, soap and remaining glycerine are removed. The reaction product sent on to the second washing stage contains only 150 to 300 ppm soap. Coming out of supply vessel 67, it is again washed with 2 to 10 l/h water at 70° to 90° C., and passed via a pipe 65 into a further separator 66, where most of the remaining glycerine, water and soap are removed, so that the mixture contains only 15 to 30 ppm soap on passing through pipe 68 into a dryer 70, run at 110° to 120° C. and 0.9 bar, whence it passes via pipe 72 and cooler 74 into a filter 76, before landing in a storage tank as the finished product.

The lower phases from separators 48, 64 and 66 are passed back into the respective former steps via pipes 49, 69 and 69', respectively Generally, when carrying out the present process, it is preferred to have the amount of alcohol introduced in reactor 14 at about 120–180%, most preferably about 150%, of the stoichiometrically required amount, and in reactor 36 at about 20–60%, most preferably about 30% of the stoichiometrically required amount. The concentration of catalyst in reactor 36 is usually about 1.1–3 times that in reactor 14, and preferably about 1.5 times. The aqueous extractants used in the process may be acidic, e.g. containing a mineral acid such as HCl, or basic, e.g. contain a base such as NaOH but preferably contain an alkaline buffer.

To obtain winter grade diesel fuel, it is wise—depending on the path of reaction taken and material used—to cool reaction mixture IV down to approximately −25° C., in order to remove alkyl esters with higher melting points in a further separator at a working temperature of −12° to −15° C. Better winter grades are obtained carrying out the initial alcoholysis with a mixture of methanol and ethanol.

For preference, the contact times in the washing and separating stages should be limited with the help of the plate separators to 1 to 20 seconds, in order to avoid effects of hydrolysis. Finally, the stirring reactor can be set at various residence times when treating different starting materials.

Although the present invention has been described in relation to particular embodiments thereof, other variations and modifications will become apparent to those skilled in the art. Those embodiments were intended to be illustrative only and were not meant to be limiting.

What is claimed is:

1. In a process for the continuous production of lower alkyl esters of higher fatty acids wherein lower alcohol and an oil phase of fatty triglycerides or natural oils or fats containing free fatty acids is subjected to catalytic transesterification at reaction temperatures of up to 100° C. in the presence of an alkaline catalyst, and glycerine, catalyst residue alcohol reactant are removed, the improvement which comprises, in sequence,
   a) introducing a reaction mixture which is pre-mixed combination of oil phase, alcohol and catalyst at reaction temperature into the top of a reactor column such that the rate of flow is less than the sinking rate of the glycerine which separates from the reaction mixture and separating free glycerine from the column transesterification product,
   b) transferring the column transesterification product which contains dissolved and dispersed glycerine, lower alkyl esters, alcohol, catalyst, oil and partially transformed oil, to a second reactor which is at reaction temperatures and conducting a further transesterification,
   c) washing the thus obtained reaction mixture with an aqueous extractant in a first separator,
   d) introducing the thus washed reaction mixture, additional alcohol and catalyst into a third reactor at reaction temperature and at a flow speed conforming to the stage a) of the process,
   e) introducing the resulting mixture into a fourth reactor and maintaining the mixture under stirring for a further transesterification, forming a reaction product have a degree of transesterification of at least 99.2%,
   f) introducing the resulting transesterification product and hot, aqueous extractant solution into a second separator and separating alcohol, glycerine, soaps formed and catalyst from the transesterification product, and
   g) drying the transesterification product.

2. The process according to claim 1, wherein the separators are plate separators which allow treatment of one phase with a second phase for a limited time contact duration to thereby substantially avoid hydrolysis.

3. The process according to claim 1, wherein the extractant solution is an aqueous solution in the acid or alkaline pH range.

4. The process according to claim 1, wherein part of the material removed from a separator is recycled to a reactor upstream thereof.

5. The process according to claim 4 wherein about 40–70% of the material removed is recycled.

6. The process according to claim 1, wherein the extraction solutions are passed through the separator countercurrent to the transesterification mixture.

7. The process according to claim 1, wherein the amount of alcohol introduced in the stage a) of transesterification is about 120 to 180%, and in stage d) of transesterification about 20 to 60%, of the stoichiometrically required amount.

8. The process according to claim 7 wherein the amount of alcohol introduced in stages a) and d) are about 150% and 30%, respectively, of the stoichiometrically required amount.

9. The process according to claim 1, wherein the concentration of catalyst in stage d) of the process is about 1.1 to 3.0 times that in stage a).

10. The process according to claim 9 in which the concentration of catalyst in stage d) is about 1.5 times that in stage a).

11. The process according to claim 1, wherein an alkaline buffer solution with a pH value of about 8 to 10 is used as an aqueous extraction solution to remove glycerine in the separator.

12. The process according to claim 1 in which the rate of flow in the reactor column is such that about 85 to 90% of the transesterification occurs therein, the reaction temperature is about 2 minutes to 2 hours and the reaction temperature is about 60° to 80° C. in the second reactor so as to increase the degree of transesterification to about 95 to 97%, the aqueous extraction temperature in the first separator is about 20° to 40° C. or about 70° to 90° C. the mixture is maintained in the fourth reactor for about 0.5 to 2 hours at about 60°–80° C., and the hot aqueous extractant solution in stage f) is at about 70° to 90° C. and constitutes about 0.25 to 10% of the material in the second separator.

13. The process according to claim 12 wherein the separators are plate separators and the rate of flow of the phases therein is such that the duration of contact is about 1 to 20 seconds.

14. The process of claim 13 wherein about 40 to 70% by weight of the material removed from a separator is recycled to a reactor upstream thereof.

15. The process according to claim 14, wherein the amount of alcohol introduced in the stage a) of transesterification is about 120 to 180%, and in stage d) of transesterification about 20 to 60%, of the stoichiometrically required amount.

16. The process according to claim 15, wherein the concentration of catalyst in stage d) of the process is about 1.1 to 3.0 times that in stage a).

* * * * *